US007341574B2

(12) United States Patent
Schreijag

(10) Patent No.: US 7,341,574 B2
(45) Date of Patent: Mar. 11, 2008

(54) VETERINARY SYRINGE

(75) Inventor: Karl Schreijag, Rottweil (DE)

(73) Assignee: Henke-Sass, Wolf GmbH, Tuttlingen (DE)

( * ) Notice: Subject to any disclaimer, the term of this patent is extended or adjusted under 35 U.S.C. 154(b) by 31 days.

(21) Appl. No.: 10/520,739

(22) PCT Filed: Mar. 10, 2003

(86) PCT No.: PCT/EP03/02444

§ 371 (c)(1),
(2), (4) Date: Jan. 7, 2005

(87) PCT Pub. No.: WO2004/007004

PCT Pub. Date: Jan. 22, 2004

(65) Prior Publication Data

US 2006/0020244 A1 Jan. 26, 2006

(30) Foreign Application Priority Data

Jul. 10, 2002 (DE) ................................ 202 10 683

(51) Int. Cl.
*A61M 5/315* (2006.01)

(52) U.S. Cl. ....................................... 604/224; 604/209

(58) Field of Classification Search ................ 604/187, 604/218, 207–211, 223–224, 233, 221
See application file for complete search history.

(56) References Cited

U.S. PATENT DOCUMENTS 2,316,095 A * 4/1943 Mead, Jr. .................... 604/209
3,504,673 A * 4/1970 Parisi ......................... 604/211
3,517,668 A * 6/1970 Brickson ..................... 604/209

FOREIGN PATENT DOCUMENTS

| | | |
|---|---|---|
| DE | 197 32 332 A1 | 2/1999 |
| FR | 2 480 126 | 10/1981 |
| FR | 2 630 330 | 10/1989 |

OTHER PUBLICATIONS (Photographs of first syringe—A) Manufactured by N.J. Phillips Pty. Ltd., Sidney, Australia, known or used by others at least as early as Dec. 2001.
(Photographs of second syringe—B) Manufactured by Henke-Sass, Wolf GmbH, Tuttlingen, Germany, HSW Roux-Revolver, known or used by others at least as early as Dec. 2001.

* cited by examiner

*Primary Examiner*—Nicholas Lucchesi
*Assistant Examiner*—Theodore J. Stigell
(74) *Attorney, Agent, or Firm*—Patterson, Thuente, Skaar & Christensen, P.A.

(57) ABSTRACT

A veterinary syringe comprises a base body for receiving a syringe barrel with a guiding element for a plunger rod that is guided therein so as to be movable in a longitudinal direction. At one end of the plunger rod, a plunger is attached that extends into the syringe barrel. The syringe further comprises a handle and an operating lever. The operating lever is connected to a guiding element that engages with a toothed rack associated with the plunger rod, and with a locking device for the plunger rod that engages with the toothed rack. The locking device acts as a locking slider disposed inside the guiding element and has an opening through which the plunger rod is guided and extends into the toothed rack from below, locking the toothed rack so as to prevent it from withdrawing.

15 Claims, 2 Drawing Sheets

VETERINARY SYRINGE

BACKGROUND

The invention relates to a veterinary syringe, comprising a base body, on the front side of which a syringe barrel receiving the medicament is arranged while a guiding element for a plunger rod that is guided therein so as to be movable in a longitudinal direction is arranged on the rear side thereof, and one end of said plunger rod, to which a plunger is attached, extends into the syringe barrel, said syringe further comprising a handle for holding the syringe, an operating lever, one end of which is pivotably attached to the lower part of the handle while the other end thereof is guided within the bottom side of the guiding element and engages with a toothed rack via a spring-biased catch, said toothed rack being disposed on the bottom side of the plunger rod, and a locking device for the plunger rod which engages with the toothed rack is provided as a locking slider disposed inside the guiding element so as to be movable in a vertical direction at the end thereof, is provided with an opening through which the plunger rod is guided and extends into the toothed rack from below, locking said toothed rack so as to prevent it from withdrawing, wherein said locking slider can be moved from the locked position into a released position for the toothed rack and can be maintained in said released position by means of an actuator.

Such known veterinary syringes, also referred to as repeater syringes, are used for mass vaccination of sheep, swine and cattle, and thus have to withstand high stresses. Above all, such syringes need to be insensitive to soiling, in particular with regard to the operating and adjusting elements provided on such syringe.

In such a known syringe, the locking device is also provided in the form of a locking slider, which is arranged within the guiding element for the plunger rod so as to be vertically movable, encompasses the plunger rod and extends into the toothed rack from below, under a spring load. The locking slider may be pushed down from above, against a spring force, so as to release the toothed catch and to allow retraction of the plunger rod. In order to maintain the locking slider in its pushed-in form, the known veterinary syringe has an annular lock which is arranged on the guiding element so as to be movable thereon in a longitudinal direction, in the region of the guiding element which extends between the base body and/or the handle, on the one hand, and the catch attached to the operating lever, on the other hand.

When the operating lever is in its resting position, i.e. at its greatest distance from the handle, the lock may be moved back toward the operating lever, or the catch attached thereto may be moved along the guiding element, with the lock pushing the locking slider down against the pressure of a spring, or then maintaining it in this position, respectively. In this condition, the plunger rod can be pulled back. If the syringe is operated again, i.e. if the operating lever is moved forward toward the handle, then the operating lever or the catch, respectively, pushes the lock forward, thus releasing the locking slider, which moves out of its locked position due to the spring load and releases the plunger rod, so that vaccinations can be carried out.

Providing the lock as a ring which is movable on the guiding element in a longitudinal direction has the disadvantage that it becomes increasingly difficult for said lock to slide on the guiding element due to the constant soiling of this area by the use of the syringe, which may eventually cause the syringe, or in particular, the lock and, thus, the locking device, to be no longer operable or releasable.

SUMMARY OF THE INVENTION

Therefore, it is an object of the invention to provide a lock or a locking device, by which the aforedescribed disadvantages of the known veterinary syringes, are avoided, said lock or locking device further being of a simpler construction or easier to manufacture and increasing the overall robustness of the veterinary syringe.

In the above-described veterinary syringe, this problem is solved by the locking slider being extended so as to protrude out of the bottom of the guiding element toward the operating lever, said extension comprising a bore, by the locking pin being provided on the operating lever, which is arranged parallel to the plunger rod, and by the locking pin extending into the bore, in the resting position of the operating lever, when the locking slider is pressed down through the guiding element all the way to the locking pin against the force of a spring.

Due to said aforedescribed design, the fixing mechanism for the locking slider for releasing the plunger rod is placed at a distance from the area of the guiding element located between the operating lever, on the one hand, and the handle or catch, respectively, on the other hand, in an area which is arranged in a protected manner in the operating lever, i.e. away from sources of soiling. According to the invention, the lock itself is provided as a simple locking pin which need not be adjusted or displaced as in the case of the prior art lock. If the locking slider is pressed down, its bore engages with the locking pin, and said locking pin does not release the locking slider again until the locking pin is pushed forward, out of its resting position by actuation of the operating lever, so that the locking slider can move up again, into the locked position, under the action of a spring.

In an advantageous embodiment of the invention, the locking slider is made of a resilient material.

This means that the locking pin may be incorporated in the operating lever in a fixed manner, so as not to be movable in its axial direction. The locking slider is then slightly bent, when pushed over the locking pin, until i is locked in position with its bore over the locking pin. This represents a comparatively simple constructive embodiment.

In another embodiment, however, the locking pin may also be arranged so as to be axially movable in the operating lever, wherein it may be pressed into its seated position by the pressure of a spring. In this case, the locking slider is not made of a flexible material, because it does not have to be able to bend, or should not bend, in this case.

The locking slider has its upper end attached to a push-button, which is supported in the guiding element and is vertically movable by the pressure of a spring. Using this push-button, the locking slider may be brought out of its locked position and is maintained in this released position by the locking pin. A spring incorporated into the push-button moves the locking slider out of the released position again and into the locked position, when the operating lever of the syringe is operated for the next injection operation.

BRIEF DESCRIPTION OF THE DRAWINGS

An embodiment of the veterinary syringe describing the invention merely by way of example is described below with reference to the Figures shown in the drawing, wherein.

DETAILED DESCRIPTION OF THE INVENTION

Figures 1, 2:
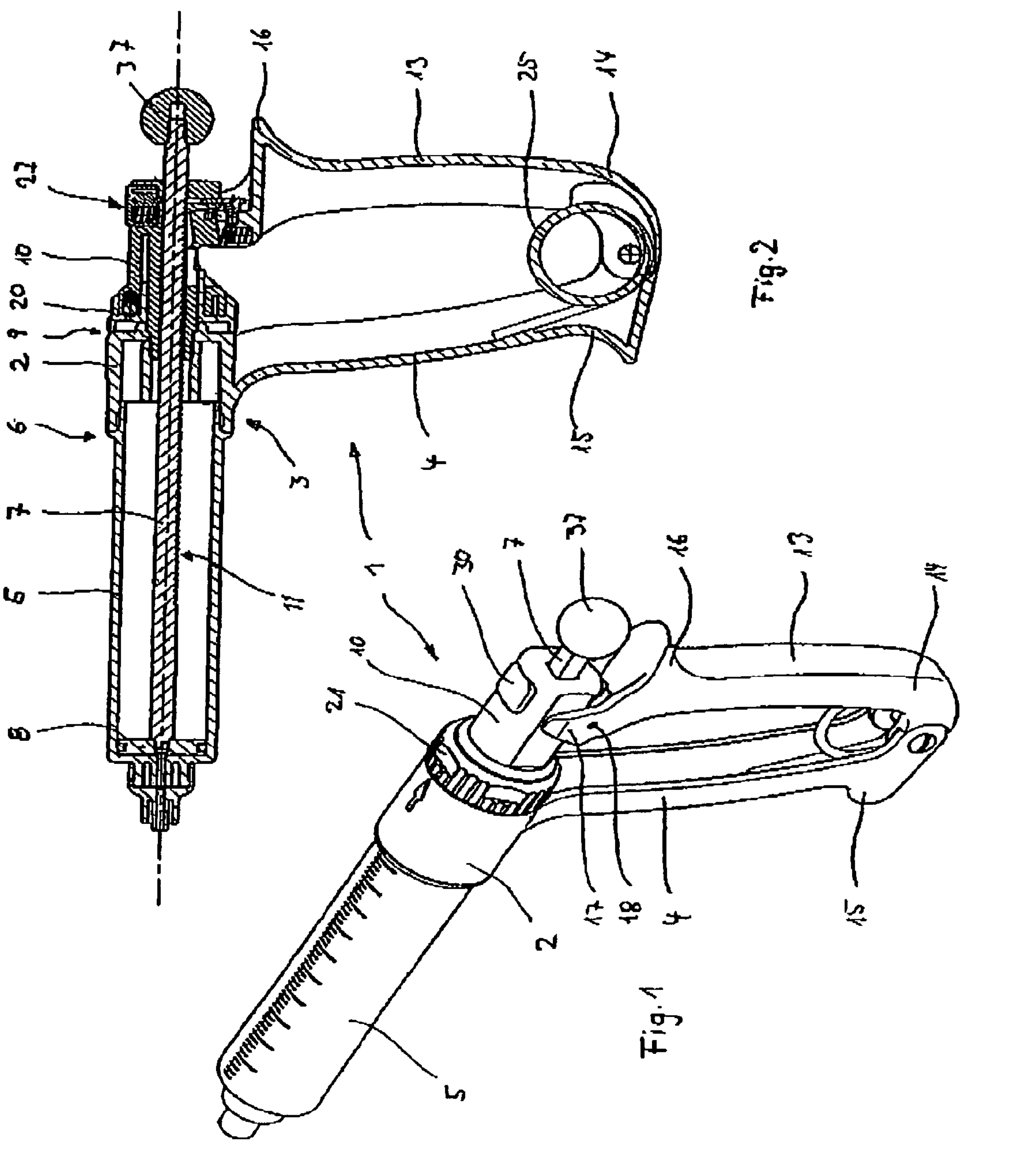
FIG. 1 shows a perspective view of the veterinary syringe.
FIG. 2 shows a vertical, longitudinal section of the veterinary syringe.
Figure 3:
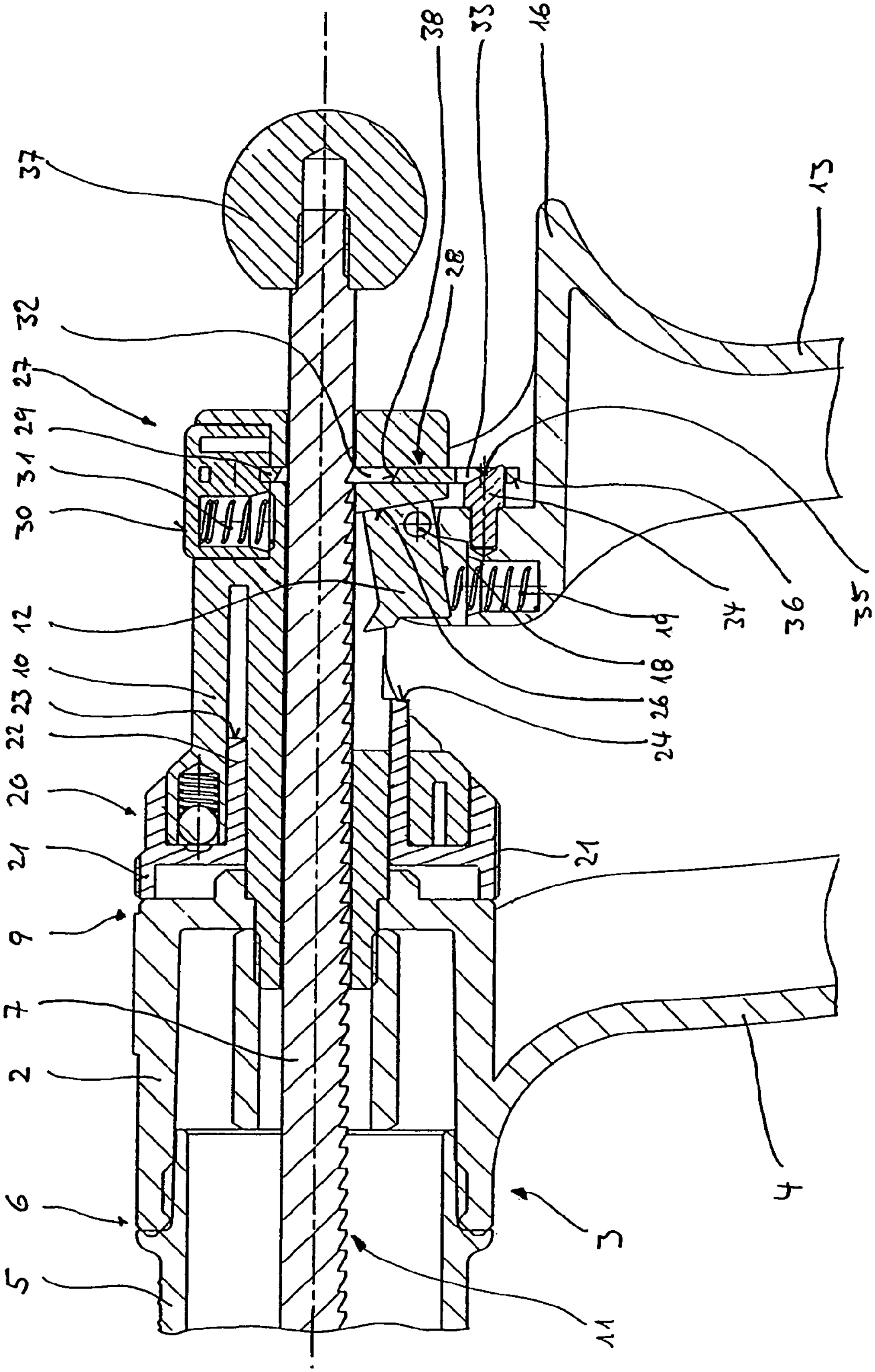
FIG. 3 shows an enlarged detail of FIG. 2.

The veterinary syringe 1 essentially comprises a base body 2 having a handle 4 arranged at the bottom surface 3 thereof, a syringe barrel 5, which is inserted at the front 6 of the base body 2 and into which a plunger rod 7 comprising a plunger 8 extends. The plunger rod 7 is held, in a lengthwise slidable manner, in a guiding element 10 arranged on the back 9 of the base body 2. At its bottom surface, the plunger rod 7 is formed as a toothed rack 11, with which a catch 12 may engage, said catch being drivable by an operating lever 13. The operating lever 13 has a first end 14 thereof pivotably attached to the free end 15 of the handle 4 and has its second end 16 guided on the guiding element 10 longitudinally of the veterinary syringe 1. In the region of the guiding element 10, the second end 16 is formed as a fork 17 which laterally embraces the guiding element 10. In this fork 17, there is provided a shaft 18, which is supported horizontally and transversely to the direction of movement of the plunger rod 7, on which shaft 18 the catch 12 is pivotably supported and is urged against the toothed rack 11 by the action of a spring 19 provided in the operating lever 13. If the operating lever 13 is moved forward in a direction toward the handle all the way to a stop, the plunger rod 7 is moved into the syringe barrel 5. Therefore, the length of movement of the operating lever 13 may be adjusted via a stroke-limiting device 20, so as to allow dosage of the quantity of the medicament to be injected. For this purpose, the stroke-limiting device 20 is integrated into the guiding element 10 and comprises an adjusting ring 21, which is arranged between the back 9 of the base body 2, on the one hand, and the guiding element 10, on the other hand, and is rotatable as well as adjustable to individual dosage levels. Said dosage levels are defined by a stop cylinder 22 which extends out of the guiding element 10, below the toothed rack 11 and opposite the catch 12, and which limits the travel of the operating lever 13 by having front faces 23 and 24, respectively, of different lengths corresponding to the dosage levels.

If the operating lever 13 is in As rearward resting position, in which it is held by a spring 25 provided at its first end 14 and cooperating with the end 15 of the handle 4, the catch 12 contacts a stop surface 26 located behind the catch 12 in the guiding element 10, said stop surface 26 holding the catch 12, against the pressure of the spring 19, in a position in which the catch 12 does not extend into the toothed rack 11.

At the rear end of the guiding element 10, there is provided a locking device 27 for locking the toothed rack 11 against inadvertent withdrawal of the plunger rod 7. For this purpose, a locking slider 29 is provided in a vertical slit 28 behind the stop surface 26 in the guiding element 10, which locking slider 29 can be pressed down via a push-button 30 against the pressure of a spring 31. In this embodiment, locking slider 29 operates in conjunction with toothed rack 11 to provide an example of a means for limiting motion of plunger rod 7. The locking slider 29 comprises an opening 32, through which the plunger rod 7 is passed, and further comprises a bore 33 arranged below said opening 32, which fully protrudes from the guiding element 10, when the push-button 30 is pushed in, so that a locking pin 34 provided in the operating lever 13, below the catch 12, and oriented horizontal and parallel to the plunger rod 7 may extend into the bore 33 and may hold the locking slider 29 in this position against the force of the spring 31. The locking pin 34 comprises an oblique front face 35, along which the locking slider 29 slides with its chamfered sliding surface 36 until the locking pin 34 extends into the bore 33 of the locking slider 29, which slightly bends back in the process. In this embodiment, locking pin 34 operates in conjunction with bore 33 to provide an example of a means for maintaining disengagement of locking slider 29 from toothed rack 11.

It would also be possible to provide the locking pin 34 to be movable in a longitudinal direction and to provide a compression spring, so that the locking pin 34 is moved back against the pressure of a spring upon pressing the push-button 30, applying a load to the chamfered sliding surface 36 of the locking slider 29, in order to subsequently move into the bore 33.

In this position of the locking slider 29, the plunger rod 7 may be retracted by a button 37 provided at one end thereof and, thus, the plunger 8 may be moved into its starting position again and, in doing so, the syringe barrel 5 may be refilled with the medicament.

If the operating lever 13 is then actuated again for the next injection and pushed forward, the locking pin 34 moves out of the bore 33 in the locking slider 29 and releases the latter which thus moves back into its starting position, wherein the locking slider 29 engages with the toothed rack 11 by the lower chamfered edge 38 of its opening 32, under the influence of the force of the spring 31. This prevents the plunger rod 7 from being retracted and, thus, an inadvertent retraction is not possible.

The invention claimed is:

1. A veterinary syringe, comprising a base body having a front side and a rear side, wherein a syringe barrel for receiving a medicament is arranged on said front side, and a guiding element for a plunger rod that is guided therein so as to be movable in a longitudinal direction is arranged on said rear side, and wherein one end of said plunger rod is coupled to a plunger and extends into said syringe barrel;

said syringe further comprising a handle for holding said syringe, an operating lever having one end pivotably coupled to a lower part of said handle, and having another end guided within a bottom side of said guiding element and engageable with a toothed rack via a catch biased towards engagement, said toothed rack being disposed on said plunger rod;

said syringe further comprising a locking device for locking a position of said plunger rod, wherein said locking device, is engageable with said toothed rack and includes a locking slider partially disposed inside said guiding element and being movable in a locking direction that is generally transverse to said longitudinal direction, wherein said locking slider is provided with an opening through which said plunger rod is guided;

wherein said locking slider can be moved from a locked position into a released position for said toothed rack by an actuator;

wherein a protruding portion of said locking slider protrudes from said guiding element toward said operating lever, and includes a bore; and wherein a locking pin is disposed on said operating lever generally transverse to said locking slider, wherein in order to maintain said locking slider in said released position, said locking pin engages with said bore when said operating lever is in a resting position and when said locking slider is pressed down through said guiding element against a biasing force.

2. A veterinary syringe according to claim 1, wherein the locking slider is made of a resilient material.

3. A veterinary syringe according to claim 1, wherein the locking pin is maintained in the operating lever in a lengthwise displaceable manner along its axial direction under the pressure of a spring.

4. A veterinary syringe according to claim 1, wherein the locking slider has its upper end attached to a push-button, which is supported in the guiding element and vertically movable against the pressure of a spring.

5. A veterinary syringe having a front side and a rear side, the syringe comprising:

a syringe barrel at said front side for receiving a medicament;

a plunger rod movable in a longitudinal direction within the syringe barrel and out the rear side;

a handle for holding the syringe;

an operating lever positioned proximate the handle and operable to move the plunger rod forward;

a toothed rack associated with the plunger rod and extending generally parallel therewith;

a locking device comprising a slider movable in a direction generally transverse to the plunger and the toothed rack and releaseably engageable with the toothed rack for restricting the motion of said toothed rack and plunger in at least a rearward direction; and a locking protrusion situated on, and movable with the operating lever, the locking protrusion engageable with the slider for releaseably securing the slider in a position disengaged with the toothed rack.

6. A veterinary syringe of claim 5 wherein when the locking slider of the locking device is disengaged with the toothed rack and the operating lever is actuated, the locking slider engages with the toothed rack.

7. The veterinary syringe according to claim 5, wherein the locking slider is made of a resilient material that flexes when engaging with the locking pin.

8. The veterinary syringe according to claim 5, wherein the locking pin is maintained in the operating lever in a lengthwise displaceable manner along its axial direction under the pressure of a spring.

9. The veterinary syringe according to claim 5, wherein the locking slider has its upper end attached to a push-button and vertically movable against the pressure of a spring.

10. A veterinary syringe having a front side and a rear side, the syringe comprising:

a syringe barrel at said front side for receiving a medicament;

a plunger rod movable in a longitudinal direction within the syringe barrel and out the rear side;

a handle for holding the syringe;

an operating lever positioned adjacent the handle and operable to move the plunger rod forward;

means for limiting motion of the plunger rod ; and means for maintaining disengagement of the means for limiting motion of the plunger rod so as to permit free movement of the plunger rod without a need to maintain application of an external force for disengaging the means for limiting motion of the plunger rod.

11. A veterinary syringe having a front side and a rear side, the syringe comprising:

a syringe body;

a syringe barrel retained by the syringe body at the front side for receiving a medicament;

a plunger rod movable in a longitudinal direction within the syringe barrel and out the rear side;

a handle portion of the syringe body for holding the syringe;

an operating member positioned proximate the handle and operable to move the plunger rod forward;

a disengageable ratcheting mechanism partially housed in the syringe body, the disengageable ratcheting mechanism associated with the plunger rod and operable to limit movement of the plunger rod to a forward direction when engaged with the plunger rod; and a locking mechanism partially housed in the syringe body and engageable with the disengageable ratcheting mechanism, the locking mechanism being operable to retain the disengageable ratcheting mechanism in a disengaged state from the plunger rod to permit the plunger rod to move in a backward direction, wherein the locking mechanism engages with the disengageable ratcheting mechanism on an exterior of the syringe body such that an interface of the locking mechanism and the disengageable ratcheting mechanism is exposed.

12. The veterinary syringe of claim 11, wherein the disengageable ratcheting mechanism includes:

a toothed rack moveable with the plunger rod;

a catching member moveable with the operating member and biased toward engagement with the toothed rack, wherein the catching member, the operable member, and the syringe body are arranged such that the operable member disengages from the toothed rack when the operating member is in a home position; and a ratcheting member biased toward engagement with the toothed rack by a biasing force, wherein a protruding portion of the ratcheting member protrudes from the syringe body and the protruding portion includes the interface that engages with the locking mechanism.

13. The veterinary syringe of claim 12, wherein the locking mechanism includes a lock control member disposed on the exterior of the syringe body and coupled with the ratcheting member, wherein the lock control member is moveable against the biasing force to effect engagement of the locking mechanism with the disengageable ratcheting mechanism.

14. The veterinary syringe of claim 11, wherein the locking mechanism includes an interface feature that is moveable with operable member, and can engage with the disengageable ratcheting mechanism to effect retention of the disengageable ratcheting mechanism when the operable member is in a home position.

15. The veterinary syringe of claim 14, wherein the interface feature disengages from the disengageable ratcheting mechanism when the operable member is moved from the home position.

* * * * *